United States Patent [19]

Wilk et al.

[11] Patent Number: 5,758,663
[45] Date of Patent: Jun. 2, 1998

[54] CORONARY ARTERY BY-PASS METHOD

[76] Inventors: Peter J. Wilk, 185 West End Ave., New York, N.Y. 10023; Jonathan Tiefenbrun, 62 Country Rd., Mamaronek, N.Y. 10543

[21] Appl. No.: 628,822

[22] Filed: Apr. 5, 1996

Related U.S. Application Data

[63] Continuation-in-part of Ser. No. 866,760, Apr. 10, 1992, Pat. No. 5,470,320.

[51] Int. Cl.⁶ .................................................. A61B 17/00
[52] U.S. Cl. ..................... 128/898; 604/174; 606/1; 606/108
[58] Field of Search ..................... 128/898; 606/1, 606/7, 8, 14, 15, 108, 151, 153; 600/108; 604/174, 180; 623/1, 11, 900

[56] References Cited

U.S. PATENT DOCUMENTS

| | | |
|---|---|---|
| 1,998,225 | 4/1935 | Dow . |
| 2,898,917 | 8/1959 | Wallace . |
| 3,683,911 | 8/1972 | McCormick . |
| 3,721,229 | 3/1973 | Panzer . |
| 3,989,033 | 11/1976 | Halpern et al. . |
| 4,133,307 | 1/1979 | Ness . |
| 4,318,401 | 3/1982 | Zimmerman . |
| 4,616,631 | 10/1986 | Takahashi . |
| 4,955,856 | 9/1990 | Phillips . |
| 4,986,825 | 1/1991 | Bays et al. . |
| 5,041,109 | 8/1991 | Abela . |
| 5,215,521 | 6/1993 | Cochran et al. . |
| 5,292,362 | 3/1994 | Bass et al. ........................ 606/214 |
| 5,452,733 | 9/1995 | Sterman et al. .................. 128/898 |
| 5,456,714 | 10/1995 | Owen .................................. 623/1 |
| 5,501,698 | 3/1996 | Roth et al. ........................ 606/205 |
| 5,569,274 | 10/1996 | Rapacki et al. ................... 128/898 |

OTHER PUBLICATIONS

Nataf et al., "Minimally Invasive...Surgical Technique", Journal of Card Surg. vol. 11, pp. 288–292 1996.
Benetti et al., "Video Assisted Coronary Bypass Surgery", Journal of Card Surg. vol. 10, pp. 620–625 1995.

*Primary Examiner*—Michael Peffley
*Attorney, Agent, or Firm*—R. Neil Sudol; Henry D. Coleman

[57] ABSTRACT

A method for performing a coronary artery bypass comprises utilizes a thoracoscope and a tubular bypass member. The method includes the step of disposing the thoracoscope in the pericardium of a patient so that the distal end of the thoracoscope projects unto the intrapericardial space of the patient. The bypass member is inserted into the intrapericardial space, and, under direct observation via the thoracoscope, the bypass member is attached to the aorta and a coronary artery of the patient so that blood flows from the aorta through the bypass member and into the coronary artery.

21 Claims, 7 Drawing Sheets

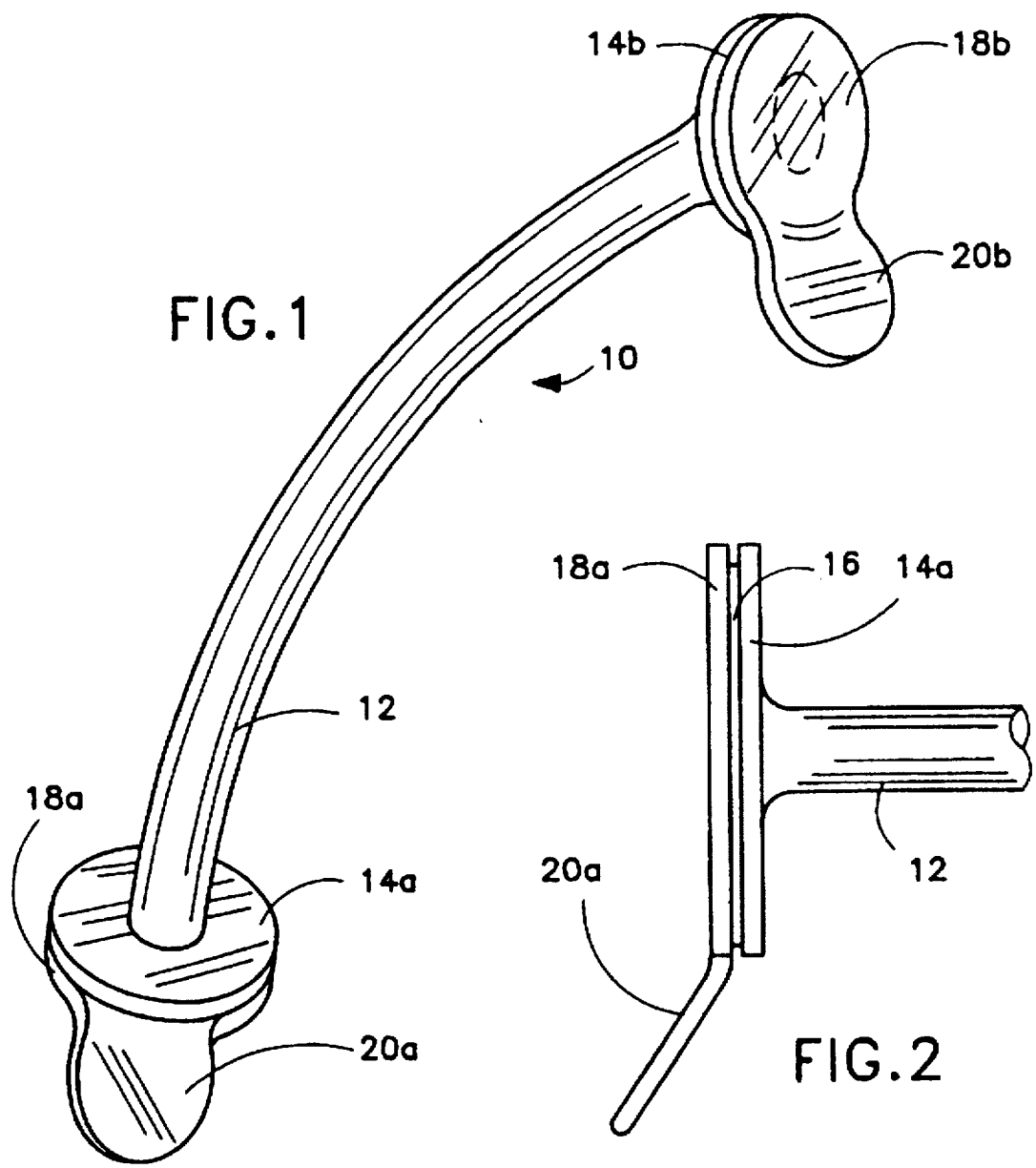
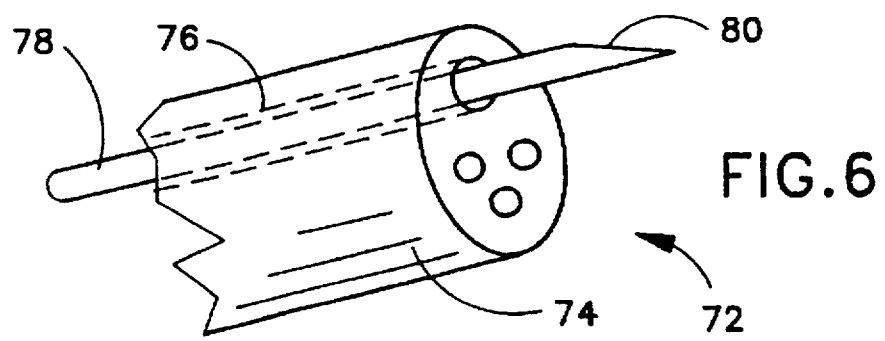

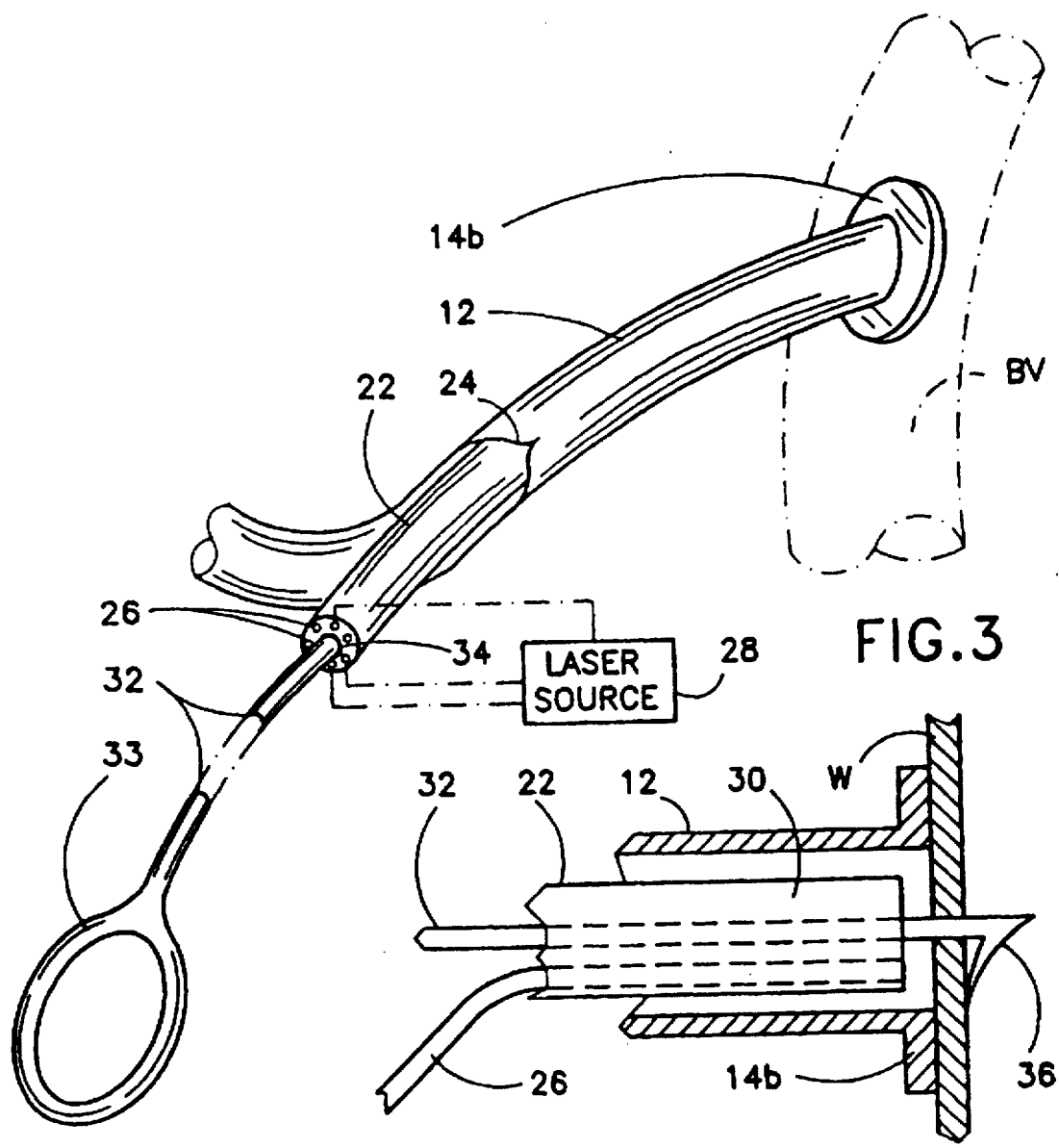
FIG.3
FIG.4
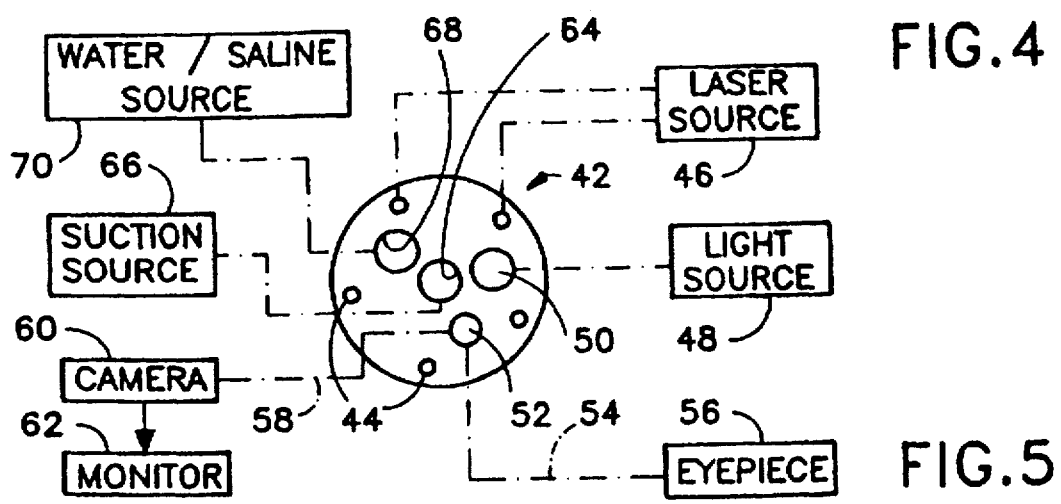
FIG.5

5,758,663

CORONARY ARTERY BY-PASS METHOD

CROSS-REFERENCE TO RELATED APPLICATION

This application is a continuation-in-part of application Ser. No. 07/866,760 filed Apr. 10, 1992 now U.S. Pat. No. 5,470,320.

BACKGROUND OF THE INVENTION

This invention relates to a method for effectuating a coronary artery bypass.

Coronary arteries frequently become clogged with plaque which at the very least impairs the efficiency of the heart's pumping action and can lead to heart attack. The conventional treatment for a clogged coronary artery is a coronary bypass operation wherein one or more venous segments are inserted between the aorta and the coronary artery. The inserted venous segments or transplants bypass the clogged portion of the coronary artery and thus provide for a free or unobstructed flow of blood to the heart.

Such conventional coronary artery bypass surgery is expensive, time-consuming, and traumatic to the patient. Hospital stay subsequent to surgery and convalescence are prolonged.

Alternative treatments have been pursued, in the treatment of heart disease, with the purpose of avoiding conventional open heart surgery and the afore-mentioned disadvantages. Such alternative treatments include angioplastic surgery in which inflatable balloons are inserted into clogged arteries and forcibly inflated at plaque sites to push the plaque aside and increase the flow areas of the respective arteries. Angioplastic surgery has had only limited success. Generally, the plaque deposits reassert themselves after a short time and the patient thus returns to the same pretreatment condition or worse.

Alternatives to open surgery have been successfully used in other areas of the body. For example, in surgically treating certain gynecological conditions or in removing gall bladders, laparoscopic surgery has proven to be an extremely beneficial approach.

Laparoscopy involves the piercing of a patient's abdominal wall and the insertion of a cannula through the perforation. Generally, the cannula is a trocar sleeve which surrounds a trocar during an abdomen piercing operation. Upon the formation of the abdominal perforation, the trocar is withdrawn while the sleeve remains traversing the abdominal wall. A laparoscopic instrument, such as a laparoscope or a forceps, is inserted through the cannula so that a distal end of the instrument projects into the abdominal cavity.

Generally, in a laparoscopic surgical procedure, three or four perforations are formed in the abdomen to enable deployment of a sufficient number of laparoscopic instruments to perform the particular surgery being undertaken. Each perforation is formed by a trocar which is surrounded by a sleeve, the sleeves or cannulas all remaining in the abdominal wall during the surgical procedure.

Prior to insertion of the first trocar and its sleeve, a hollow needle is inserted through the abdominal wall to enable pressurization of the abdominal cavity with carbon dioxide. This insufflation procedure distends the abdominal wall, thereby producing a safety space above the patient's abdominal organs.

Laparoscopic surgery provides several advantages over conventional incision-based surgery. The laparoscopic perforations, in being substantially smaller than the incisions made during conventional operations, are less traumatic to the patient and provide for an accelerated recovery and convalescence. Hospital stays are minimized. Concomitantly, laparoscopic surgery is less time consuming and less expensive than conventional surgery for correcting the same problems.

Similar procedures are undertaken in endoscopic thoracic surgery. The endoscopic observation instrument is called a "thoracoscope" instead of a "laparoscope." Generally, thoracoscopic surgery is directed to the lungs and the thoracic cavity.

OBJECTS OF THE INVENTION

An object of the present invention is to provide a new method for performing a coronary artery by-pass operation.

Another object of the present invention is to provide such a method which is less invasive and less traumatic to the patient than conventional bypass surgery.

An additional object of the present invention is to provide such a method which is less expensive than conventional by-pass surgery.

A more particular object of the present invention is to provide such a method which is undertaken through the chest wall but which minimizes incisions through the chest wall.

These and other objects of the present invention will be apparent from the drawings and detailed descriptions herein.

SUMMARY OF THE INVENTION

A method for performing a coronary artery bypass comprises, in accordance with the present invention, the steps of (a) providing a thoracoscope and a tubular bypass member, (b) disposing the thoracoscope in the pericardium of a patient so that the distal end of the thoracoscope projects into the intrapericardial space of the patient, (c) inserting the bypass member into the intrapericardial space, and (d) under direct observation via the thoracoscope, attaching the bypass member to the aorta and a coronary artery of the patient so that blood flows from the aorta through the bypass member and into the coronary artery.

According to a specific embodiment of the present invention, the bypass member is passed along the aorta and through an aperture in the aorta into the intrapericardial space. In that case, of course, the aperture is formed prior to passage of the bypass member through the aperture. Pursuant to this embodiment of the present invention, the method may further comprise the step of passing a guide wire along the aorta and through the wall of the aorta into the intrapericardial space, the bypass member being subsequently passed over the guide wire.

In accordance with an alternative embodiment of the invention, the bypass member is inserted into the intraperi-cardial space through a cannula traversing the pericardium. In the event that a guide wire is inserted through the aorta and a free end of the guide wire ejected through the sidewall of the aorta into the intrapericaridal space, the bypass member is introduced over a free end of the guide wire in the intrapericardial space. One end of the bypass member, the upstream end, may be then attached to the wall of the aorta about the point of exit of the guide wire. A downstream end of the bypass member is subsequently attached to the selected coronary artery.

Where the bypass member is inserted into the intrapericardial space through a cannula traversing the pericardium, apertures may be formed in the aorta and the coronary artery subsequently to attachment of the bypass member to the aorta and the coronary artery. The apertures may be formed by inserting the distal end portion of a cutting instrument first into the intrapericardial space and then into the bypass member. Alternatively, the apertures may be formed by inserting the distal end portion of the cutting instrument initially through the aorta, the distal end portion of the cutting instrument being inserted into the bypass member upon formation of the aperture in the aorta.

Where the bypass member is inserted into the intrapericardial space through a cannula traversing the pericardium, the method further comprises the step of manipulating the bypass member in the intrapericardial space via a surgical instrument having a distal end inserted into the intrapericardial space via a cannula, for example, the same cannula used for introducing the bypass member into the intrapericaridal space.

Pursuant to another feature of the present invention, the bypass member is provided at one end with a flange, the step of attaching including the step of connecting the flange to one of the aorta and the coronary artery. The step of connecting may include the step of gluing or laser welding the flange to one of the aorta and the coronary artery.

According to another feature of the present invention, the method includes the step of forming apertures in the aorta and the coronary artery. This step may be performed by operating a contact laser type instrument.

A method for performing a coronary artery bypass comprises, in accordance with another conceptualization of the present invention, the steps of (a) providing a tubular bypass member and a cannula, (b) disposing the cannula in the pericardium of a patient so that the distal end of the cannula projects into the intrapericardial space of the patient, (c) inserting the bypass member through the cannula into the intrapericardial space, and (d) attaching the bypass member to the aorta and a coronary artery of the patient so that blood flows from the aorta through the bypass member and into the coronary artery.

Pursuant to another feature of the present invention, the method includes the step of forming apertures in the aorta and the coronary artery subsequently to attachment of the bypass member to the aorta and the coronary artery. As discussed above, forming the apertures may include the step of inserting a distal end portion of a cutting instrument initially into the intrapericardial space and subsequently into the bypass member. Alternatively, the apertures may be formed by inserting a distal end portion of the cutting instrument initially through the aorta, the distal end portion of the cutting instrument being inserted into the bypass member upon formation of the aperture in the aorta.

In accordance with yet another embodiment of the present invention, the bypass member is manipulated in the intrapericardial space via a surgical instrument having a distal end inserted into the intrapericardial space via the cannula.

A method in accordance with the present invention greatly reduces the expense of coronary surgery, as well as the trauma to the patient and the convalescence required after the by-pass operation. Only a few small incisions or puncture wounds in the patient are necessary.

BRIEF DESCRIPTION OF THE DRAWING

FIG. 1 is a perspective view, on an enlarged scale, of a tubular vascular bypass member in accordance with the present invention.

FIG. 2 is a partial side elevational view, on a larger scale, of the vascular bypass member of FIG. 1.

FIG. 3 is a schematic perspective view, on an enlarged scale, of the vascular bypass member of FIGS. 1 and 2, showing an excision instrument inserted into the bypass member for excising a portion of an artery wall.

FIG. 4 is a cross-sectional view of the vascular bypass member and excision instrument of FIG. 3.

FIG. 5 is a distal end elevational view, on an enlarged scale, of a modified excision instrument in accordance with the present invention.

FIG. 6 is a partial perspective view, on an enlarged scale, of the distal end of another excision instrument in accordance with the present invention.

Figures 7, 8:
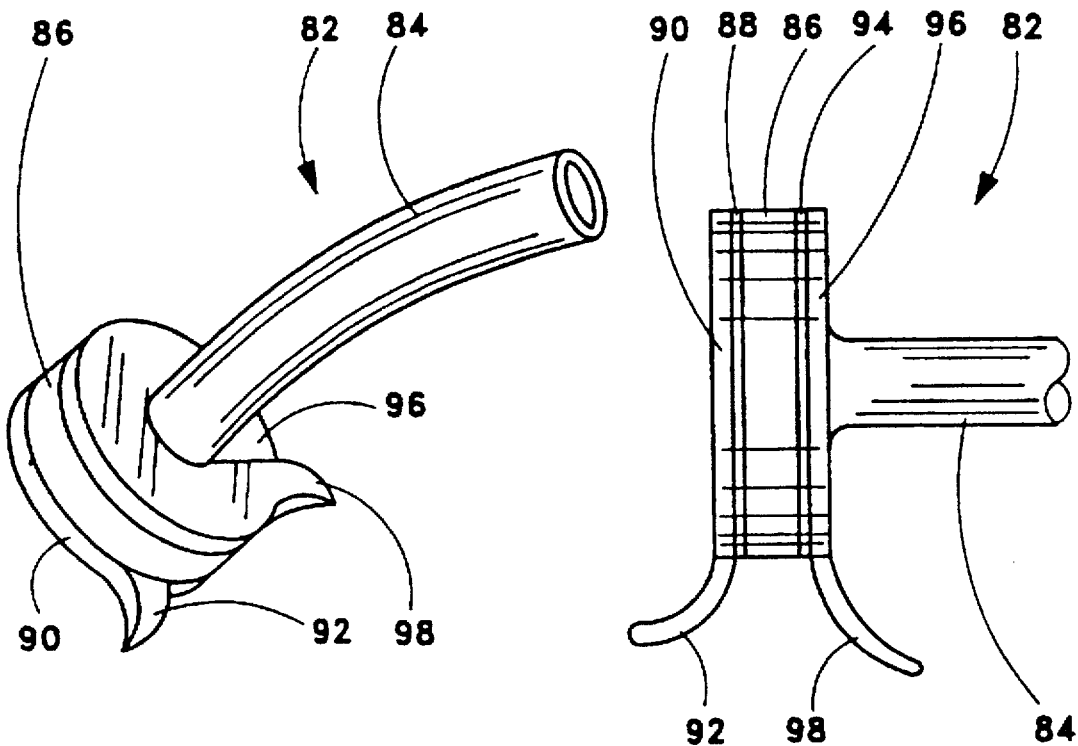
FIG. 7 is a partial perspective view, on an enlarged scale, of a tubular member for use in a gastrostomy procedure.
FIG. 8 is a partial side elevational view, on a larger scale, of the tubular member of FIG. 7.

In the drawings, reference signs which are repeated designate the same structure.

DETAILED DESCRIPTION

As illustrated in FIGS. 1 and 2, a device 10 for use in providing a patient with a vascular bypass comprises a tubular member 12 made of any nontoxic biocompatible material used in conventional surgical applications. Tubular member 12 is provided at opposite ends with integral annular flanges 14a and 14b. Flanges 14a and 14b in turn are each provided, on a surface facing opposite tubular member 12, with a layer 16 of a nontoxic biocompatible adhesive.

Device 10 further comprises cover sheets or membranes 18a and 18b removably attached to flanges 14a and 14b for protecting the adhesive layers 16. Each cover sheet 18a and 18b is provided with a respective pull tab 20a or 20b.

In using vascular bypass device 10, pull tab 20a or 20b is grasped to remove cover sheet 18a or 18b from its respective flange 14a or 14b, thereby exposing the underlying adhesive layer 16. The adhesive layer 16 of selected flange 14a or 14b is then pressed against a wall of a vein or, more likely, an artery so that flange 14a or 14b adheres to the artery wall.

As illustrated in FIG. 3, an elongate flexible excision instrument 22 is then inserted into tubular member 12 via an incision 24 in the wall thereof. Incision 24 may be formed during the surgical procedure or may be previously provided in tubular member 12, e.g., during manufacture.

Alternatively, excision instrument 22 may be inserted through tubular member 12 from a proximal end.

Excision instrument 22 is longitudinally traversed by a plurality of optical fibers 26 which are connected at a proximal end of the instrument to a laser source 28. Source 28 generates a laser beam having a frequency or wavelength absorbed by vascular tissue.

Optical fibers 26 are angularly equispaced about the periphery of excision instrument 22. Upon an attachment of tubular member 12 to a wall W (FIG. 4) of an artery or blood vessel BV (FIG. 3) and an insertion of excision instrument 22 into tubular member 12 so that a distal end 30 of the instrument is juxtaposed to wall W, as illustrated in FIG. 4, laser source 28 is energized to transmit electromagnetic radiation of a predetermined frequency along optical fibers 26 to wall W. Excision instrument 22 is turned about a longitudinal axis (not illustrated) through an angular distance essentially equal to the angle between optical fibers 26, thereby forming a circular closed circuit incision in arterial wall W.

Prior to the activation of laser source 28, a rod 32 having a finger loop 33 at a proximal end is inserted in a distal direction through a longitudinal channel 34 in excision instrument 22 so that a hook 36 at the distal end of the rod pierces through arterial wall W, as depicted in FIG. 4. Hook 36 serves the function of holding the excised tissue section against the distal end 30 of excision instrument 22 and thereby preventing that piece of the arterial wall W from falling away into artery BV. Accordingly, upon an activation of laser source 28 and a turning of excision instrument 22 about its longitudinal axis, rod 32 is pulled in the proximal direction, i.e., away from arterial wall W, so that hook 36 clamps the excised arterial wall section against distal end 30 of excision instrument 22.

Upon the attachment of vascular bypass device 10 to arterial wall W and the removal of excision instrument 22 together with the excised arterial wall section clamped thereto, the other end of vascular bypass device 10 is attached to another segment of artery BV in an identical procedure, thereby essentially completing the bypass operation.

As illustrated in FIG. 5, a modified excision instrument 42 is longitudinally traversed by a plurality of angularly equispaced optical fibers 44 which are connected at a proximal end of the instrument to a laser source 46. A light source 48 is connected to another optical fiber or fiber optic bundle having an output port 50. Light source 48 generates visible electromagnetic radiation transmitted to output port 50 for illuminating a section of arterial wall inside tubular member 12. Reflected radiation is conducted through an inlet port 52 along an ordered fiber optic bundle 54 to an eyepiece 56. Alternatively, the reflected radiation is transmitted along an optic fiber bundle 58 to a camera 60, for example, a charge coupled device (CCD), which is connected to a video monitor 62 for displaying a video image of the vascular tissues enclosed at the distal end of tubular member 12 during a vascular bypass procedure.

Excision instrument 42 is further provided with a first longitudinally extending channel 64 for enabling the securing of an excised tissue section to the distal end of excision instrument 42. Channel 64 is operatively connected to a suction source or vacuum generator 66 for generating a negative pressure at the distal end of excision instrument 22. Alternatively, a rod with a hook such as rod 32 with hook 36 (FIGS. 2 and 4) may be inserted through channel 64.

Excision instrument 22 has another longitudinal channel or duct 68 connected to a water or saline source 70 for ejecting water through tubular member 12 in the event that channel 64 is traversed by rod 32.

As depicted in FIG. 6, another excision instrument 72 for use with tubular member 12 comprises a flexible body member 74 provided with a peripheral channel 76 which is longitudinally traversed by a rod 78 having a scalpel type blade 80 at a distal end. Blade 80 is used to form a circular incision in an arterial wall, e.g., wall W, during a turning of body member 74 about a longitudinal axis.

It is to be noted that excision instrument 22, 42 or 72 may take the form of an angioscope modified in accordance with principles set forth herein.

As illustrated in FIGS. 7 and 8, a device 82 for use in a gastrostomy procedure comprises a tubular member 84 made of any nontoxic biocompatible material used in conventional surgical applications. Tubular member 84 is provided at a distal end with an integral annular flange 86. Flange 86 is in turn provided, on a surface facing opposite tubular member 84, with a layer 88 (FIG. 8) of a nontoxic biocompatible adhesive removably covered with a protective film 90. Film 90 has a pull tab extension 92. On a side opposite adhesive layer 88 and film 90, flange 86 is provided with another layer 94 of nontoxic biocompatible adhesive temporarily covered with a protective release strip 96. Release strip 96 has a pull tab extension 98.

Figure 9A:
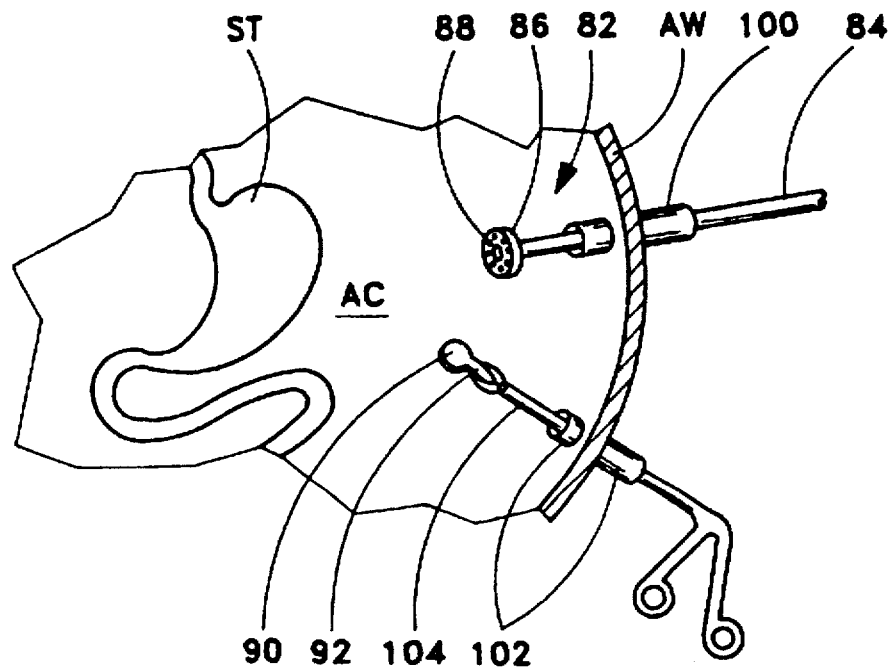
FIGS. 9A–9C are diagrams showing successive steps in the use of the tubular member of FIGS. 7 and 8 to perform a gastrostomy.

As illustrated in FIG. 9A, the distal end of tubular member 84 is inserted into a patient's abdominal cavity AC through a trocar sleeve or laparoscopic cannula 100 which has been previously inserted in the an abdominal wall AW of the patient. Through another trocar sleeve or laparoscopic cannula 102, a grasping forceps 104 is inserted. Tubular member 84 and forceps 104 are manipulated from outside the patient to remove protective film 90 from flange 86, thereby exposing adhesive layer 88.

Figure 9B:
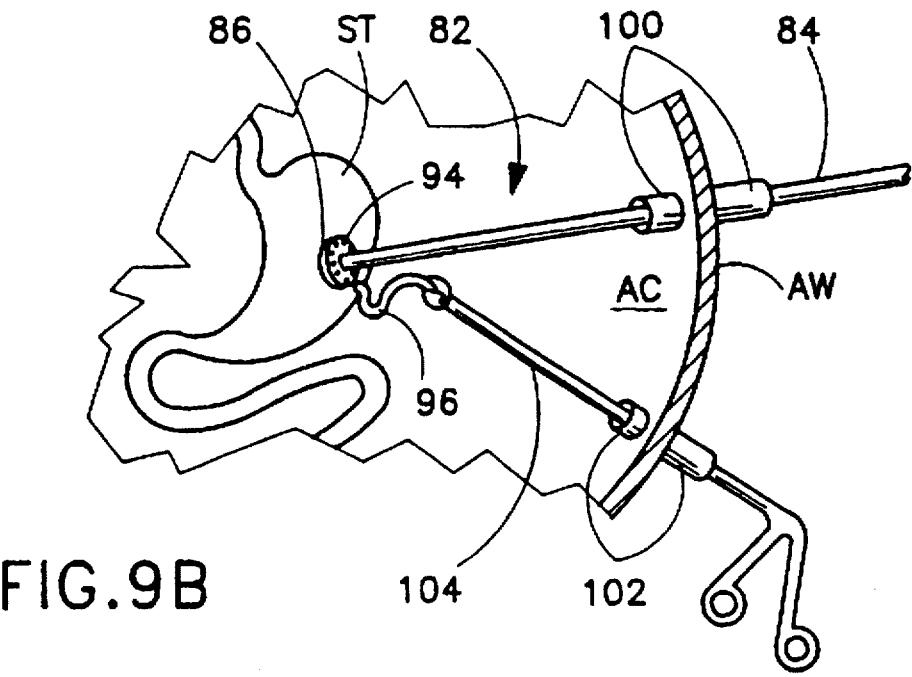

As depicted in FIG. 9B, tubular member 84 is then manipulated to press flange 86 against a wall of a stomach ST so that the flange is attached thereto by adhesive layer 88. Upon the attachment of flange 86 to the stomach wall, forceps 104 is used to remove protective release strip 96 from the posterior side of flange 84. At that juncture, cannula 100 is removed from abdominal wall AW and, in the event that abdominal cavity AC had been filled with carbon dioxide or other biologically inert gas, the gas is allowed to escape from the abdominal cavity, whereupon abdominal wall approaches stomach ST. Tubular member 84 is then pulled in the proximal direction, i.e., out of abdominal cavity AC and through abdominal wall AW, until posterior adhesive layer 94 is brought into contact with abdominal wall AW, as illustrated in FIG. 9C.

Figure 9C:
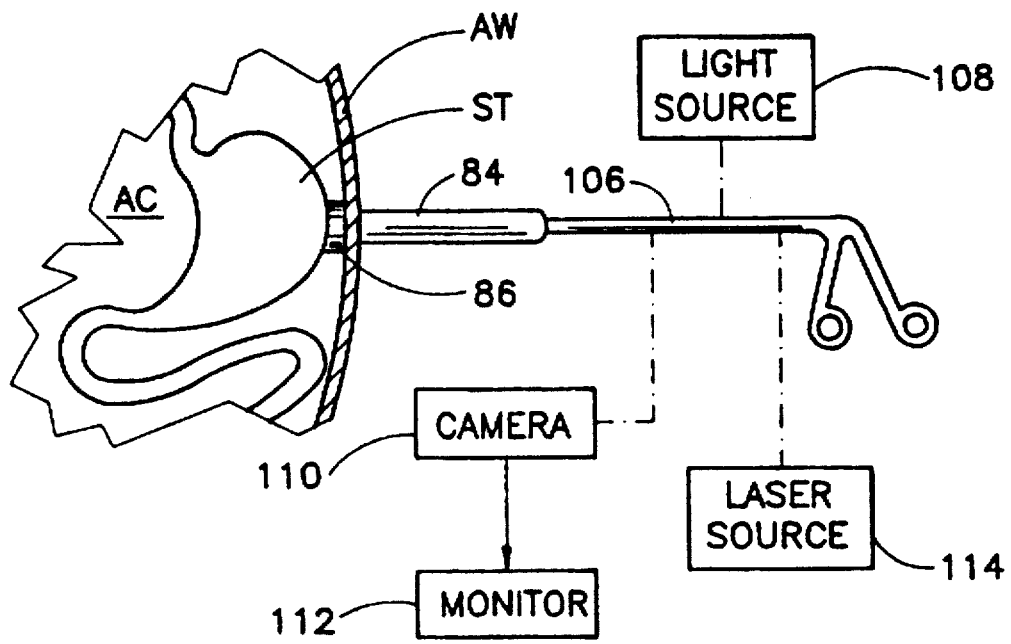

As further shown in FIG. 9C, an excision instrument 106 is then inserted through tubular member 84. Excision member 106 may take any form described hereinabove. For example, excision instrument 106 may be operatively connected to a light source 108, a camera 110 and a monitor 112 for enabling a visual inspection of a section of the stomach wall enclosed inside the distal end of tubular member 84 and flange 86. A laser source 114 may be connected to the instrument for use in forming a circular incision in the stomach wall at the distal end of tubular member 84.

Upon a removal of instrument 106 and the excised stomach wall section, as described hereinabove, a tube (not shown) may be inserted through tubular member 84 for purposes of draining stomach ST or feeding a supply of nutrients thereto.

Figure 10A:
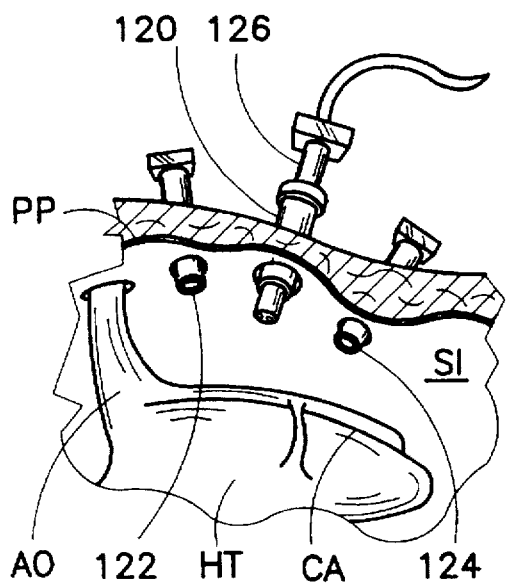
FIGS. 10A–10F are diagrams showing successive steps in a pericardioscopic coronary bypass operation in accordance with the present invention.

As illustrated in FIG. 10A, in a pericardioscopic coronary bypass operation, a plurality of laparoscopic type cannulas 120, 122, 124 are disposed in a chest wall CW of a patient so that the cannulas traverse a parietal pericardium PP and extend into an intrapericardial space SI between the heart HT of the patient and the surrounding parietal pericardium PP. Cannulas 120, 122, 124 are placed pursuant to conventional thoracoscopic procedures, i.e., with a trocar and between the ribs of the patient. If necessary, carbon dioxide gas may be introduced into intrapericardial space SI for insufflating that space to ensure sufficient room to complete the bypass operation, as described hereinafter. Insufflation is maintained by conventional valving procedures.

A distal end portion of a thoracoscope 126 is inserted into intrapericardial space SI through a cannula 120. This enables the bypass operation to proceed under direct visual observation. As customary in thoracoscopic and laparoscopic procedures, the thoracoscope 126 is coupled to a video monitor for displaying a two-dimensional image of heart HT, the aorta AO, and at least one coronary artery CA.

The pericardioscopic coronary bypass operation is based in part on intervascular bypass principles discussed hereinabove. Accordingly, a flexible tubular bypass member 128 (Fig. 10B) made of nontoxic biocompatible material is inserted into intrapericardial space SI via cannula 122. Bypass member 128 includes a tubular middle portion 130 provided at opposite ends with integral annular flanges 132. Flanges 132 in turn are each provided, on a surface facing opposite tubular portion 130 or opposite the other flange, with a respective layer (not designated) of a nontoxic biocompatible adhesive. Bypass member 128 further comprises cover sheets or membranes 134 removably attached to flanges 132 for protecting the adhesive layers, for example, during insertion into intrapericardial space SI via cannula 122. Each cover sheet 134 is provided with a respective pull tab 136.

Figure 10B:
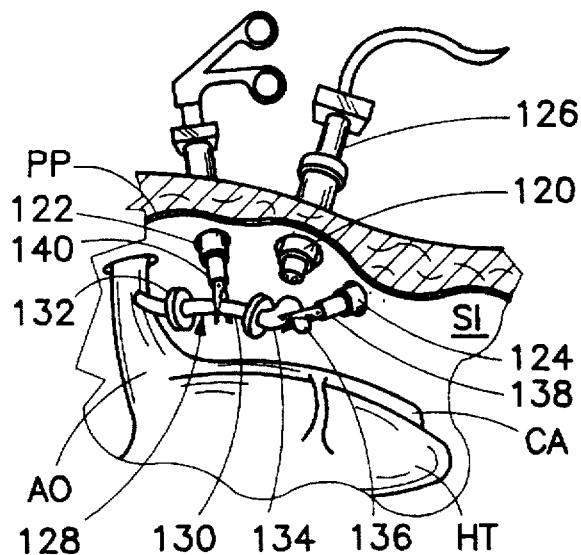

As illustrated in Fig. 10B, one of the pull tabs 136 is grasped via a laparoscopic forceps 138, the distal end of which is inserted into intrapericardial space SI via cannula 124. At the same time, the bypass member 128 is held by another laparoscopic graspers or forceps 140 which is introduced into intrapericardial space SI via cannula 122. Forceps 138 and graspers 140 are manipulated from outside the patient to remove the respective cover sheet or membrane 134 from its respective flange 132, thereby exposing the underlying adhesive layer. The removed cover sheet or membrane 134 is extracted from intrapericardial space SI by forceps 138 via cannula 124. The flange 132 with the exposed adhesive layer is then pressed against a wall of coronary artery CA or aorta AO so that the flange adheres to the arterial wall. Bypass member 128 is maneuvered in this operation via graspers 140 and/or forceps 138. The remaining protective cover sheet or membrane 134 is then removed in a similar procedure and the adhesive layer of the respective flange 132 pressed against the other blood vessel, whether aorta AO or coronary artery CA, to form the bridge or bypass connection shown in FIG. 10C.

Figure 10C:
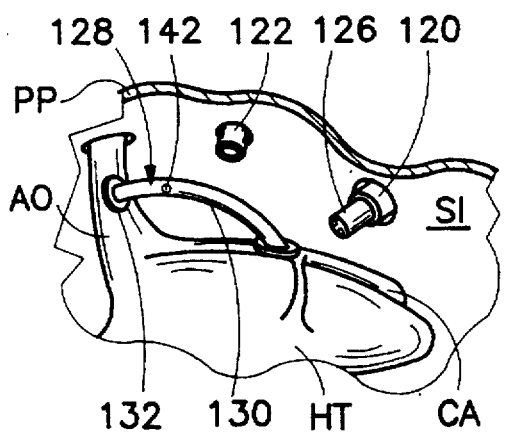

As further illustrated in FIG. 10C, tubular portion 130 of bypass member 128 is provided with an incision or aperture 142 for the insertion of an excising instrument. Aperture 142 may be formed in tubular portion 130 prior to insertion of bypass member 128 into intrapericardial space SI, e.g., during manufacture. Alternatively, a laparoscopic scalpel (not shown) or other cutting instrument may be used to form aperture 142 upon the attachment thereof to coronary artery CA and aorta AO.

Figure 10D:
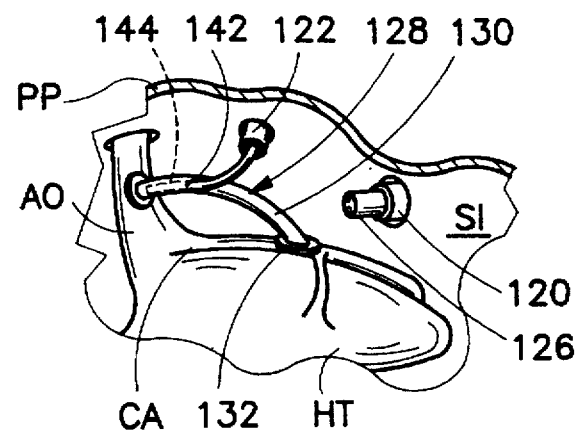

As shown in FIG. 10D, an elongate flexible excising instrument 144 is inserted into intrapericardial space SI via cannula 122 or 124 and then into bypass member 128 via incision or aperture 142. Excising instrument 144 may take any form described hereinabove with reference to FIGS. 3–6.

Figure 10E:
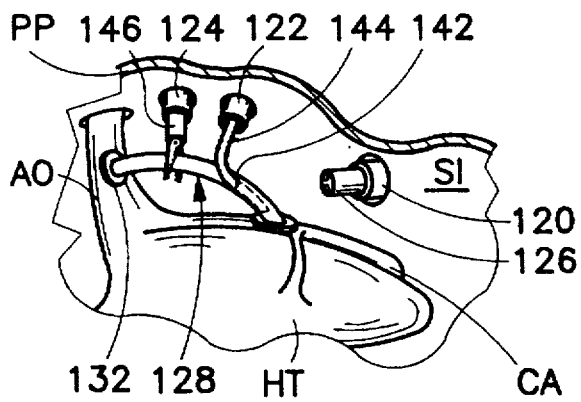

Excising instrument 144 is used to cut a closed circuit incision in the wall of aorta AO to remove a section of that wall surrounded by bypass member 128. Upon the removal of the arterial wall section, a laparoscopic clamping forceps 146 inserted through one of the cannulas 122 or 124 may be actuated to temporarily occlude bypass member 128, as illustrated in FIG. 10E, thereby blocking blood flow from the aorta through tubular portion 130 and into intrapericardial space SI. Excising instrument 144 is subsequently operated to remove a section of wall of coronary artery AO, from within bypass member 128. As described hereinabove, the excised arterial wall sections are held to the distal end of the excising instrument and removed from the vascular system of the patient.

Figure 10F:
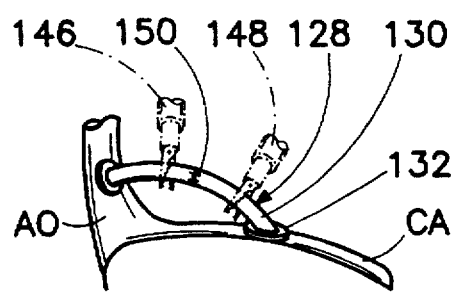

As illustrated in FIG. 10F, a clip or forceps 148 may be used to occlude tubular portion 130 of bypass member 128 proximately to coronary artery CA upon the formation of an access opening into that organ, as described above. Aperture 142 is then closed, e.g., via sutures 150 and/or a patch (not shown). Such a patch may be attached to bypass member 128 by adhesive and/or by laser welding, as described in U.S. Pat. No. 5,254,113, the disclosure of which is hereby incorporated by reference.

Figure 11:
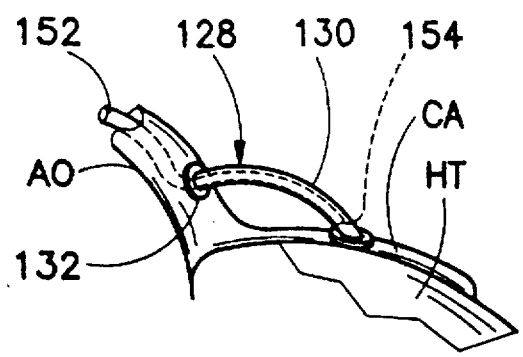
FIG. 11 shows a step in a modification of the operation of FIGS. 10A–10F.

FIG. 11 depicts a step in a variation of the pericardioscopic coronary artery bypass procedure described above with reference to FIGS. 10A–10F. Upon attachment of tubular flexible bypass member 128 to aorta AO and coronary artery CA, an excising instrument 152 is deployed via the vascular system of the patient. More particularly, as in angioplastic surgery, excising instrument 152 is passed through a femoral artery (not shown) and an iliac artery (not shown) to the aorta AO. Instrument 152 has an operative tip 154 as described above with reference to FIGS. 3–6. If instrument 152 is a laser, it may take the form of a contact laser.

Upon the arrival of operative tip 154 of instrument 152 at the point of attachment of bypass member 128 to the aorta AO, instrument 152 is operated to excise or remove a disk-shaped section of arterial wall contiguous with the lumen of tubular portion 130. Locating the lumen of bypass member 128 may be accomplished via an ultrasonic probe (not shown) inserted with instrument 152 through the vascular system of the patient. Alternatively, if flanges 132 incorporate magnetic material, the location of bypass member 152 may be detected via a magnetic sensor (not shown) also inserted with instrument 152 through aorta AO.

As illustrated in FIG. 11, a distal end portion of excising instrument 152 is inserted through tubular portion 130 of bypass member 128 upon the formation of an opening in the wall of aorta AO. Instrument 152 is then utilized to form an aperture in coronary artery CA so that the lumen of bypass member 128 communicates with coronary artery CA.

FIGS. 12A–12E depict a modification of the periocardioscopic coronary artery bypass operation discussed hereinabove with reference to FIG. 11. A wire 156 passed through aorta AO is used to guide excising instrument 152 to the lumen of bypass member 128 upon the attachment thereof to aorta AO and to coronary artery CA. The guiding of the excising instrument 152 along wire 156 is implemented pursuant to well known techniques of angiographic surgery. FIGS. 12A–12E depict steps in the procedure prior to the insertion of excising instrument 152.

Figure 12A:
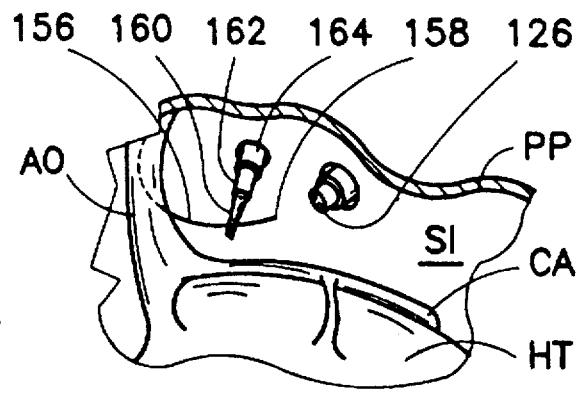
FIGS. 12A–12E are diagrams showing successive steps in another pericardioscopic coronary bypass operation in accordance with the present invention.
Figure 12B:
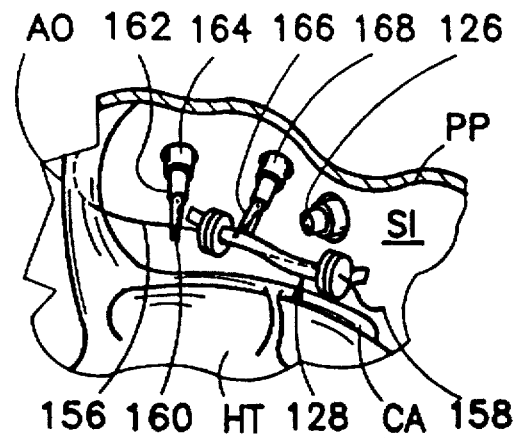
Figure 12C:
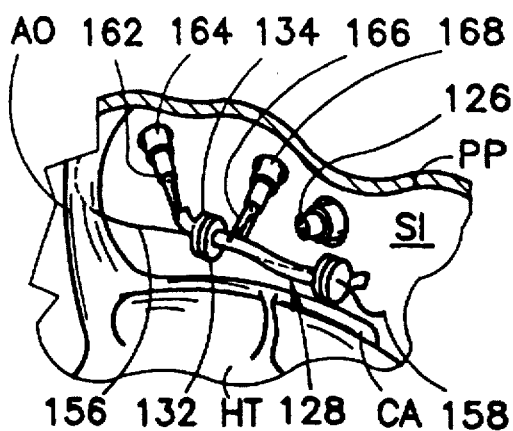

As shown in FIG. 12A, distal tip 158 of guide wire 156 is pushed through the wall of aorta AO in a predetermined region proximate to coronary artery CA. Jaws 160 of a laparoscopic type forceps 162 inserted into intrapericardial space SI via a cannula 164 are actuated to grasp wire 156 and hold it for insertion through bypass member 128 upon introduction thereof into intrapericardial space SI via a cannula 168. Another laparoscopic forceps or graspers 166 is inserted into intrapericardial space SI through cannula 168 and used to manipulate bypass member 128, as illustrated in FIG. 12B. Distal tip 158 of wire 156 may be pushed through cover sheets or membranes 134, with the cover sheets or membranes being removed subsequently by forceps 162, as illustrated in FIG. 12C. Alternatively, one or both cover sheets or membranes 134 may be removed by forceps 162 prior to the passing of wire 156 through bypass member 128.

Figure 12D:
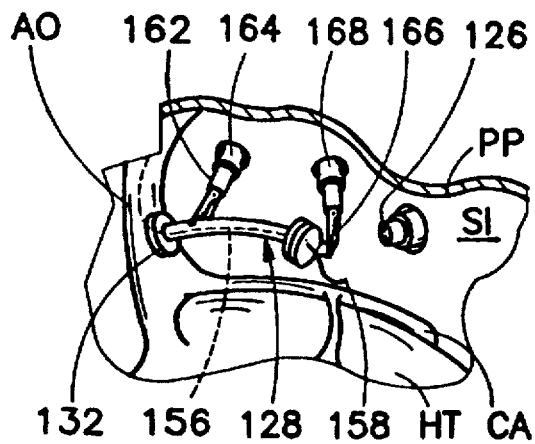
Figure 12E:
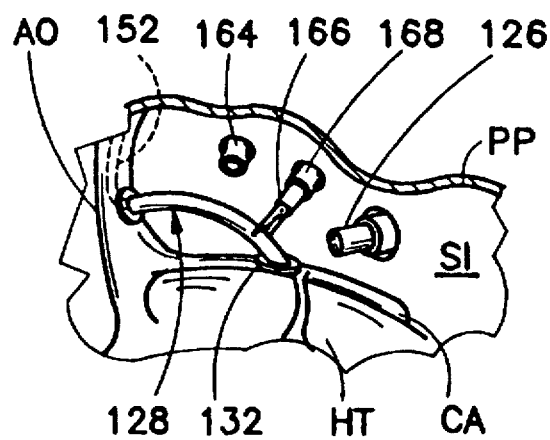

Upon the removal of one protective cover sheet 134, as illustrated in FIG. 12C, the associated flange 132 is pressed against aorta AO about the point of exit of wire 156. The pressure may be applied by forceps 162 (FIG. 12D). Alternatively, another instrument (not shown) may be employed for ensuring the adhesion of the selected flange 132 to the aortic wall. Upon the fastening of one end of bypass member 128 to aorta AO, graspers 166 are used to detach the protective cover sheet 134 from the other end of bypass member 128, as depicted in FIG. 12D. Bypass member 128 is then attached at a downstream end to coronary artery CA, as shown in FIG. 12E. Thoracoscope 126 is used in the procedure of FIGS. 12A-12E to enable direct observation by a surgeon. Wire 156 is used to guide excising instrument 152 (FIGS. 11 and 12E) to the lumen of bypass member 128 at the upstream end thereof.

Figure 13A:
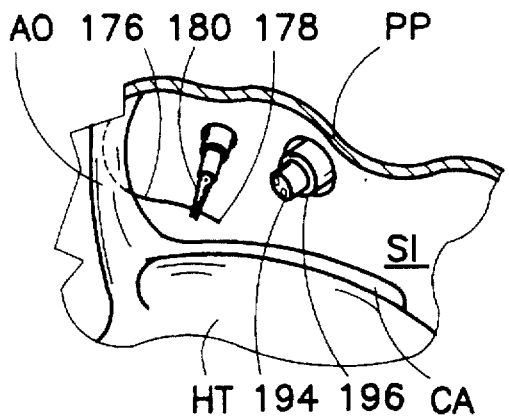
FIGS. 13A–13D are diagrams showing successive steps in yet another pericardioscopic coronary bypass operation in accordance with the present invention.
Figure 13B:
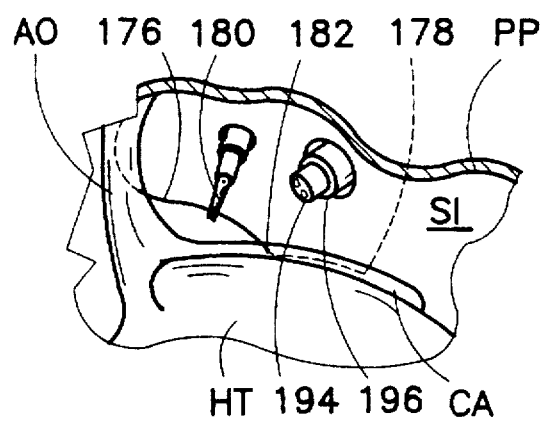
Figure 13C:
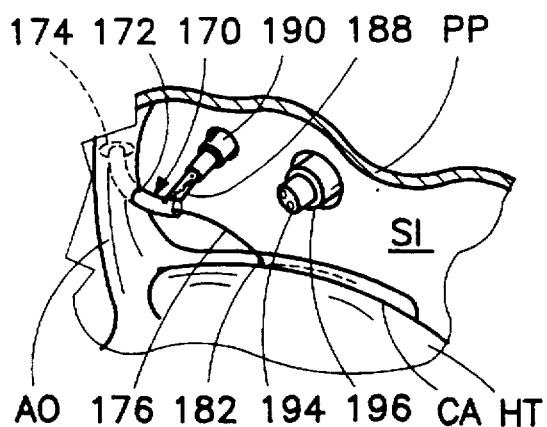
Figure 13D:
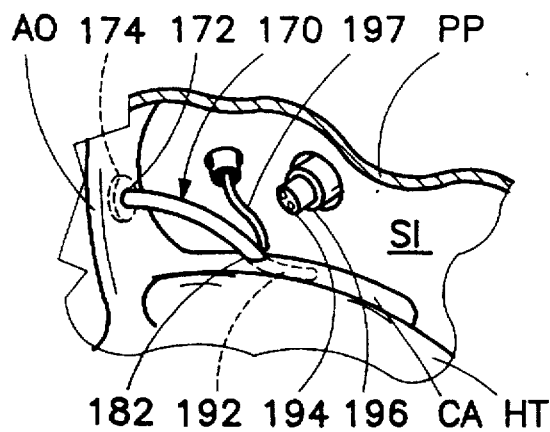
Figure 14:
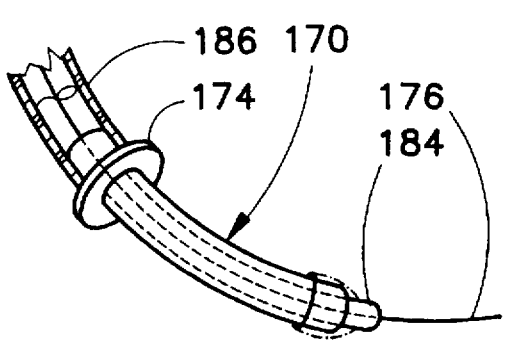
FIG. 14 is a schematic perspective view of a coronary bypass device for use in implementing the pericardioscopic coronary bypass operation of FIGS. 13A–13D.

According to another embodiment of a periocardioscopic coronary artery bypass operation illustrated diagrammatically in FIGS. 13A-13D, a bypass member 170 (FIGS. 13C and 13D) is passed along aorta AO and through an aperture 172 in the aorta into intrapericardial space SI. Bypass member 170, as shown in FIGS. 13C, 13D, and 14, has a flange 174 only at an upstream end. This flange 174 abuts against an inner surface of aorta AO, as depicted in FIG. 13D, upon completion of the periocardioscopic coronary artery bypass operation.

To guide bypass member 170 through the vascular system of the patient to a predetermined upstream bypass junction (at aperture 172), a wire 176 (FIG. 13A) is passed through aorta AO, as discussed above with reference to FIG. 12A. Upon a pushing of a distal end portion 178 of wire 176 from aorta AO at the predetermined upstream bypass junction (at aperture 172), that distal end is guided by a laparoscopic graspers 180 to a downstream bypass junction 182 in coronary artery CA, where the distal end of wire 176 is inserted into the coronary artery.

Upon the disposition of distal end portion 178 of wire 176 so that it extends from aorta AO to coronary artery CA, as illustrated in FIGS. 13A and 13B, aperture 172 is formed in the aortic wall by an excising instrument 184 as described hereinabove with reference to FIGS. 3-6 and 11. Excising instrument 184 is guided to the location of aperture 172, i.e., the location of the upstream bypass junction in aorta AO by wire 176.

Upon the formation of aperture 172 in aorta AO, bypass member 170 is pushed through aorta AO along guide wire 176 and out through aperture 172, as shown in FIG. 13C. To that end, a cylindrical pusher 186 may surround excising instrument 184 and engage bypass member 170 at flange 174 thereof, as illustrated in FIG. 14. Excising instrument 184 traverses bypass member 170, as well as pusher 186 (see FIG. 14). A laparoscopic grasping forceps 188 inserted through a cannula 190 may be used to pull bypass member 170 from aorta AO through aperture 172, as further shown in FIG. 13C. Additionally, or alternatively, grasping forceps 188 may be used to temporarily occlude bypass member 170 upon an extrusion thereof through aperture 172, thereby stemming blood loss through aperture 172 and bypass member 170.

Upon the formation of aperture 172, excising instrument 184 is withdrawn from pusher 186, in order to remove the excised aortic wall section from the vascular system of the patient. Upon subsequent reinsertion, the excising instrument 184 is used to form an aperture at downstream bypass junction 182 in coronary artery CA. Of course, grasping forceps 188 is actuated to release bypass member 170 to permit the traversal thereof by excising instrument 184. Again, wire 176 serves to guide excising instrument 184 to junction 182. Upon the formation of an aperture in coronary artery CA at junction 182, pusher 186 is manipulated to shift bypass member 170 in a distal direction so that a distal end portion 192 thereof enters coronary artery CA, as depicted in FIG. 13D.

All of the steps discussed above in relation to FIGS. 13A-13D are performed under direct observation enabled by a thoracoscope 194 inserted into intrapericardial space SI via a laparoscopic type cannula 196. As further illustrated in FIG. 13D, a controlledly flexible tubular glue applicator 197 may be used to seal the aperture at downstream junction 182, as well as aperture 172. Flexure of glue applicator 197 may be implemented by wires passing down opposite sides of the applicator, as in conventional endoscopes.

Figure 15:
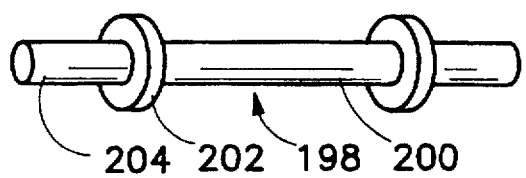
FIG. 15 is a schematic side perspective view of a coronary bypass stent in accordance with the present invention.
Figure 16:
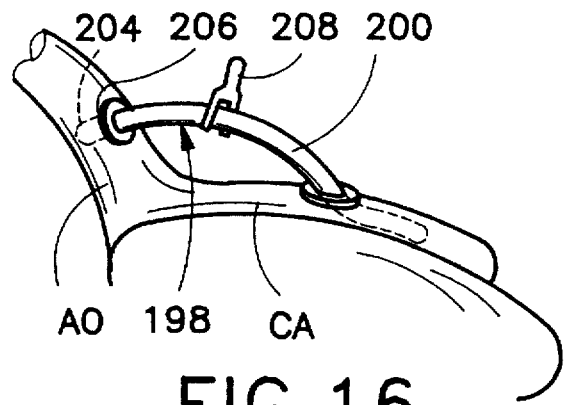
FIG. 16 is a diagram showing a step in the use of the coronary bypass stent of FIG. 15.

Other variations in a periocardioscopic coronary artery bypass operation will occur to those skilled in the art based on the present disclosure. For instance, aperture in aorta AO and coronary artery CA may be formed prior to the attachment of a bypass member, whether by an intravascularly inserted excising instrument or a thoracoscopically inserted excising instrument. Such a procedure utilizes a bypass stent 198 (FIG. 15) having a tubular body portion 200, a pair of flanges 202 at opposite ends of the body portion 200, and a pair of tubular extensions 204 made of a dissolvable material such as salt or sugar. Upon the formation of an arterial aperture 206 (FIG. 16), bypass stent 198 is manipulated via a laparoscopic type instrument (not shown) to insert one of the tubular extensions 204 through the aperture. A clamp 208 (FIG. 16) may be applied to tubular body portion 200 to temporarily block blood flow upon insertion of an extension 204 into aorta AO or coronary artery CA. Upon the formation of an aperture at the other bypass junction point, the remaining dissolvable extension is inserted through the newly formed aperture. Of course, a surgeon will take care to properly predetermine the locations of the bypass junctions in aorta AO and coronary artery CA prior to excising sections from the walls thereof. As discussed above, flanges 202 are provided with respective layers of a suitable adhesive. In addition, the attachment of bypass flanges to aorta AO and coronary artery CA may be enhanced by the application of laser radiation via an optical fiber inserted through a trocar sleeve or cannula. The optical fiber may be self guided or aimed with the aid of a graspers.

Adhesives which may be utilized with the present invention include cyanoacrylic compositions and fibrin glues or sealants such as TISSUCOL™ and BERIPLAST™. Other adhesives will be known to one skilled in the art.

Although the invention has been described in terms of particular embodiments and applications, one of ordinary skill in the art, in light of this teaching, can generate additional embodiments and modifications without departing from the spirit of or exceeding the scope of the claimed invention. For example, a tubular bypass member in accordance with the present invention may be a graft fabricated from organic tissue instead a synthetic biocompatible material. In addition, the organic biocompatible adhesive may be applied to terminal flange-like appurtenances of the vascular bypass device via a brush immediately prior to application. In most instances, however, the releaseable protective strip or cover element is considered to be easier and safer to use.

It is to be noted, furthermore, that the method described herein may be used not only for vascular bypass operation or a gastrostomy but also for attaching tubular access port elements to other hollow organs of a patient, such as the gall bladder (cholecystostomy), the urinary bladder (cystostomy), the small intestine (jejeunostomy), and the cecum (tube cecostomy).

The flanges of a tubular access device may be attached to a hollow organ in some cases by other techniques such as laser welding, ultrasonic welding, cauterization, or suturing.

It is to be additionally noted that the removal of a disk- or wedge-shaped section of organ wall may be accomplished by using a controlled laser to essentially vaporize the wall section. The vapor remnant may then be removed, if necessary, from the bypass junction by sucking the vapors through the tubular bypass member.

Accordingly, it is to be understood that the drawings and descriptions herein are proferred by way of example to facilitate comprehension of the invention and should not be construed to limit the scope thereof.

What is claimed is:

1. A method for performing a coronary artery bypass, comprising:
    providing a thoracoscope and a tubular bypass member;
    disposing said thoracoscope in a pericardium of a patient so that a distal end of said thoracoscope projects into an intrapericardial space of the patient;
    inserting said bypass member into said intrapericardial space;
    under direct observation via said thoracoscope, attaching said bypass member to an aorta and a coronary artery of the patient; and
    after at least partially attaching said bypass member to the aorta and the coronary artery, forming apertures in the aorta and the coronary artery in regions of attachment of said bypass member to the aorta and the coronary artery to enable blood flow from the aorta through said bypass member and into the coronary artery.

2. The method defined in claim 1 wherein said bypass member is passed along the aorta and through an aperture in the aorta into said intrapericardial space, further comprising the step of forming said aperture prior to passage of said bypass member through said aperture.

3. The method defined in claim 2, further comprising the step of passing a guide wire along the aorta and through a wall of the aorta into said intrapericardial space, said bypass member being subsequently passed over said guide wire.

4. The method defined in claim 2, further comprising the step of passing a guide wire along the aorta and through a wall of the aorta into said intrapericardial space, said bypass member being inserted into said intrapericardial space through a cannula traversing said pericardium, said bypass member being inserted over a free end of said guide wire in said intrapericardial space.

5. The method defined in claim 1 wherein said bypass member is inserted into said intrapericardial space through a cannula traversing said pericardium.

6. The method defined in claim 5 wherein said step of forming apertures includes the step of inserting a distal end portion of a cutting instrument initially into said intrapericardial space and subsequently into said bypass member.

7. The method defined in claim 5 wherein said step of forming apertures includes the step of inserting a distal end portion of a cutting instrument initially through the aorta, said distal end portion of said cutting instrument being inserted into said bypass member upon formation of the aperture in said aorta.

8. The method defined in claim 5, further comprising the step of manipulating said bypass member in said intrapericardial space via a surgical instrument having a distal end inserted into said intrapericardial space via said cannula.

9. The method defined in claim 1 wherein said bypass member is provided at one end with a flange, said step of attaching including the step of connecting said flange to one of said aorta and said coronary artery.

10. The method defined in claim 9 wherein said step of connecting includes the step of gluing said flange to said one of said aorta and said coronary artery.

11. The method defined in claim 9 wherein said step of connecting includes the step of laser welding said flange to said one of said aorta and said coronary artery.

12. The method defined in claim 1 wherein said step of forming apertures includes the step of operating a contact laser type instrument to form said apertures.

13. A method for performing a coronary artery bypass, comprising:
    providing a tubular bypass member and a cannula;
    disposing said cannula in a pericardium of a patient so that a distal end of said cannula projects into an intrapericardial space of the patient;
    inserting said bypass member through said cannula into said intrapericardial space; and
    attaching said bypass member to an aorta and a coronary artery of the patient; and
    after at least partially attaching said bypass member to the aorta and the coronary artery, forming apertures in the aorta and the coronary artery in regions of attachment of said bypass member to the aorta and the coronary artery to enable blood flow from the aorta through said bypass member and into the coronary artery.

14. The method defined in claim 13 wherein said step of forming apertures includes the step of inserting a distal end portion of a cutting instrument initially into said intrapericardial space and subsequently into said bypass member.

15. The method defined in claim 13 wherein said step of forming apertures includes the step of inserting a distal end portion of a cutting instrument initially through the aorta, said distal end portion of said cutting instrument being inserted into said bypass member upon formation of the aperture in said aorta.

16. The method defined in claim 13, further comprising the step of manipulating said bypass member in said intrapericardial dial space via a surgical instrument having a distal end inserted into said intrapericardial space via said cannula.

17. A method for performing a coronary artery bypass, comprising:
    providing a thoracoscope and a tubular bypass member;
    disposing said thoracoscope in a pericardium of a patient so that a distal end of said thoracoscope projects into an intrapericardial space of the patient;
    passing a guide wire along an aorta of the patient and through a wall of the aorta into said intrapericardial space;

passing said bypass member over said guide wire into said intrapericardial space; and under direct observation via said thoracoscope, attaching said bypass member to the aorta and a coronary artery of the patient so that blood flows from the aorta through said bypass member and into the coronary artery.

18. The method defined in claim 17 wherein said bypass member is passed along the aorta and through an aperture in the aorta into said intrapericardial space, further comprising forming said aperture prior to passage of said bypass member through said aperture.

19. A method for performing a coronary artery bypass, comprising:

providing a thoracoscope and a tubular bypass member, exactly one flange or ring being located at and fixed to one end of said bypass member;

disposing said thoracoscope in a pericardium of a patient so that a distal end of said thoracoscope projects into an intrapericardial space of the patient;

inserting said bypass member into said intrapericardial space; and under direct observation via said thoracoscope, attaching said bypass member to an aorta and a coronary artery of the patient so that blood flows from the aorta through said bypass member and into the coronary artery, the attaching of said bypass member including (a) placing said flange or ring along one side of one of said aorta and said coronary artery and (b) connecting said flange or ring to said one side so that an opposite side of said one of said aorta and said coronary artery is substantially free of any flange or ring of said bypass member.

20. The method defined in claim 19 wherein the connecting of said flange or ring to said one side includes gluing said flange ring to said one side.

21. The method defined in claim 19 wherein the connecting of said flange or ring to said one side includes laser welding said flange or ring to said one side.

* * * * *